United States Patent [19]

Nishino et al.

[11] 4,276,128
[45] Jun. 30, 1981

[54] HUMIDITY SENSING ELEMENT OF ELECTRIC CAPACITANCE CHANGE TYPE AND METHOD OF PRODUCING SAME

[75] Inventors: Atsushi Nishino; Akihiko Yoshida; Nobukuni Ogino, all of Kadoma, Japan

[73] Assignee: Matsushita Electric Industrial Co., Ltd., Osaka, Japan

[21] Appl. No.: 14,382

[22] Filed: Feb. 21, 1979

[30] Foreign Application Priority Data

| Feb. 20, 1978 [JP] | Japan | 53-18950 |
| Mar. 15, 1978 [JP] | Japan | 53-30422 |
| Mar. 15, 1978 [JP] | Japan | 53-30423 |
| Mar. 15, 1978 [JP] | Japan | 53-30424 |
| Mar. 15, 1978 [JP] | Japan | 53-30425 |

[51] Int. Cl.$^3$ .................................... H01G 9/05
[52] U.S. Cl. ....................... 204/38 A; 204/37 R; 73/335; 29/570
[58] Field of Search ............ 204/37 R, 38 A; 427/80, 427/226; 73/335; 29/570

[56] References Cited

U.S. PATENT DOCUMENTS

| 3,376,481 | 4/1968 | Klerer | 204/38 A X |
| 3,987,676 | 10/1976 | Bennewitz | 73/336.5 |
| 4,038,159 | 7/1977 | Nishino et al. | 204/38 A |

FOREIGN PATENT DOCUMENTS

| 44-11639 | 5/1969 | Japan . |
| 947857 | 1/1964 | United Kingdom . |
| 1393901 | 5/1975 | United Kingdom . |

*Primary Examiner*—Delbert E. Gantz
*Assistant Examiner*—William Leader
*Attorney, Agent, or Firm*—Lowe, King, Price & Becker

[57] ABSTRACT

A device comprising a dielectric oxide film formed by anodization of a surface region of a valve metal body, a semiconductive metal oxide layer porously formed on the dielectric oxide film, and a gas permeable electrode layer formed on the semiconductive metal oxide layer with the interposal of a gas permeable carbon layer therebetween. The semiconductive metal oxide layer is formed by pyrolysis of a metal salt solution so as to be, microscopically, only partially in contact with the dielectric oxide film. After forming of the electrode layer, the device is immersed in boiling water and/or kept in a high temperature high humidity atmosphere for an adequate amount of time to stabilize the semiconductive metal oxide layer, resulting in that the semiconductive metal oxide layer has a multiplicity of microscopic crevices and that the device becomes quite stable in the relation between humidity and electrostatic capacitance of the device.

14 Claims, 26 Drawing Figures

10 μm

10 μm

HUMIDITY SENSING ELEMENT OF ELECTRIC CAPACITANCE CHANGE TYPE AND METHOD OF PRODUCING SAME

BACKGROUND OF THE INVENTION

This invention relates to a humidity sensing element which comprises a dielectric oxide layer formed by anodization of a valve metal body and a porous layer of semiconductive metal oxide with an electrode layer coated thereon and exhibits changes in its electrostatic capacitance with changes in humidity in the surrounding atmosphere, and a method of producing the same.

Measurement of humidity with high precision is still difficult compared with measurement of other physical variables of the atmosphere such as temperature and pressure. However, the need for easy and accurate measurement of humidity is increasing in many fields such as food industries, agriculture, air conditioning and medical service either to control humidity or to accommodate something to humidity.

As a general trend, preference has been given to electrical methods of measuring humidity. One of the now prevailing methods of this category is the use of a deliquescent salt, such as lithium chloride, which undergoes a change in its ionic conductivity with a change in its moisture content, and another is the use of a hygroscopic substance, such as magnetite or a silicon semiconductor, which exhibits a change in its electrical resistance as it adsorbs and desorbs moisture. However, humidity sensors embodying these methods, i.e. humidity sensors utilizing ionic conductivity, exhibit considerable drifting of the indications with the passage of time by reason of polarization. Besides, electrical indications of these humidity sensors are influenced also by the adsorption of various gaseous substances other than moisture. Furthermore, these humidity sensors are not fully satisfactory in their responsiveness, mode of hysteresis and the width of humidity range they can cover.

Another category of conventional electric humidity sensors comprise a filament of an organic material such as human hair, nylon or polystyrene in combination with a strain gauge or microswitches so as to detect the deformation of the filament caused by adsorption and desorption of moisture. However, these humidity sensors are unsatisfactory in their accuracy, responsiveness, hysteresis and heat resistance. A still different type of humidity sensor utilizing swelling of a synthetic resin containing fine particles of an electronically conductive material such as carbon or a metal is low in sensitivity, unsatisfactory in responsiveness and weak to high temperature. A further example of known methods is the use of a porous alumina layer for detecting a change in humidity as a change either in electric capacitance or impedance of the alumina layer resulting from adsorption of moisture in the pores, or desorption therefrom. A drawback of this method is a considerable drifting of the dependence of the capacitance or the impedance on humidity with the passage of time.

Highly accurate measurement of humidity is possible by means of an apparatus using the principle of α-ray absorption and transmission, but such an apparatus is too large-scaled and too costly to be of general use.

Also there is an apparatus to convert the indications of a traditional wet and dry bulb hygrometer into electrical signals, but this apparatus, too, is large-scaled and unsuitable for measurement of humidity in narrow spaces.

Thus, humidity sensing devices and apparatus now on the market all have certain drawbacks in their functional characteristics, resistance to environmental conditions, price, stability over a long period of time and/or convenience for usage and maintenance: none of them is fully satisfactory in every respect.

U.S. patent application Ser. No. 912,714 filed June 5, 1978, by Nishino et al, now U.S. Pat. No. 4,217,623, discloses a humidity sensing element of an electrostatic capacitance change type, comprising a substrate of a valve metal, a dielectric oxide layer formed by anodization of a surface region of the substrate and a gas permeable counter-electrode layer formed on the dielectric layer preferably using a semiconductive metal oxide such as manganese dioxide as an inner half of the counter-electrode layer, on the condition that, microscopically, the counter-electrode layer is only partially in contact with the dielectric layer.

SUMMARY OF THE INVENTION

It is an object of the present invention to provide a humidity sensing element of an electrostatic capacitance change type, which element is high in accuracy and sensitivity and quick in response and can be made very small in size.

It is another object of the invention to provide a method of producing a humidity sensing element of the described type, which method gives a product excellent in functional characteristics as a humidity sensing element and little in the variations of the relation between humidity and electrostatic capacitance with the passage of time.

A humidity sensing element according to the invention comprises a metal body which is of a valve metal and serves as an electrode, a dielectric oxide film formed by anodization of a surface region of the metal body, a semiconductive metal oxide layer porously formed on the dielectric oxide film, a gas permeable layer of carbon formed on at least a portion of the outer surface of the semiconductive metal oxide layer and a gas permeable and electronically conductive layer which is formed on the carbon layer and comprises a metal powder dispersed in a synthetic resin matrix. Microscopically, the semiconductive metal oxide layer is only partially in contact with the dielectric oxide film and has a plurality of microscopic crevices of which depth is substantially equal to the thickness of the semiconductive metal oxide layer.

Preferably, the metal body is of tantalum, aluminum or titanium, and the semiconductive metal oxide layer is of manganese dioxide, lead oxide and/or ruthenium oxide. A tantalum body and a manganese dioxide layer is the most preferable combination. Colloidal graphite is preferred as the material for the carbon layer, and preferably use is made of a metallic paint such as a silver paint comprising either an acrylic resin or a fluorocarbon resin as binder to form the outermost conductive layer.

According to the invention, a humidity sensing element of the above stated construction is produced by a method comprising the steps of anodizing a valve metal body to form a dielectric oxide film on the surface of the valve metal body, porously forming a semiconductive metal oxide layer on the dielectric oxide film by thermal decomposition of an aqueous solution comprising a thermally decomposable metal salt on the surface of the dielectric oxide film, forming a gas permeable layer of carbon on at least a portion of the outer surface of the semiconductive metal oxide layer, forming a gas permeable and electronically conductive layer on the carbon layer by applying a paint comprising a metal powder and a synthetic resin as a binder to the outer surface of the carbon layer, and subjecting the product of the foregoing steps to a damping treatment at an elevated temperature with control of the temperature and humidity for the treatment and the duration of the treatment.

Preferably, the damping treatment is accomplished by maintaining the semifinished sensing element in a vapor phase atmosphere above about 80° C. in temperature and above about 90% in relative humidity for a predetermined amount of time, or by immersing the semifinished sensing element in boiling water for a predetermined amount of time, or by first immersing the semifinished sensing element in boiling water for a predetermined amount of time and then maintaining the same element in the aforementioned vapor phase atmosphere for another predetermined amount of time.

After solidification of the metal paint but before the damping treatment, the semifinished sensing element is preferably treated with an organic polar solvent.

Using tantalum as the metal valve body, preferably the anodization of the metal body is accomplished at an anodizing voltage not higher than 150 volts, and also preferably the semiconductive metal oxide layer is formed by the use of a manganese nitrate solution having a density not higher than 1.7.

DESCRIPTION OF THE PREFERRED EMBODIMENTS

Figure 1:
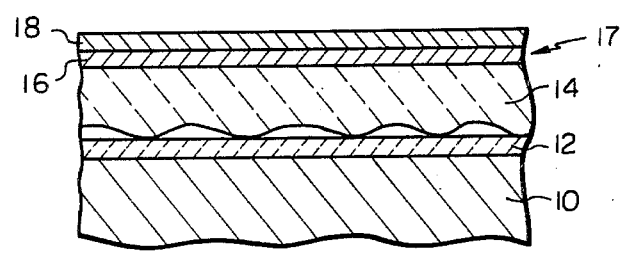
FIG. 1 shows a fundamental construction of a humidity sensing element according to the invention in an explanatorily enlarged sectional view.
Figure 2:
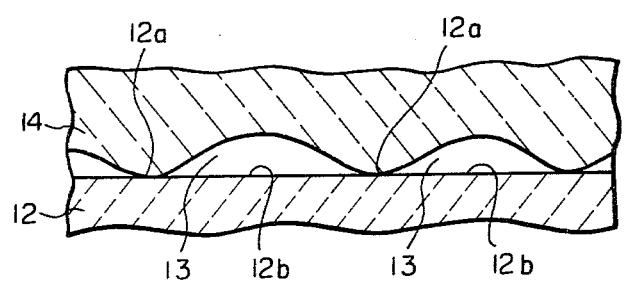
FIG. 2 is a partial enlargement of FIG. 1.

FIGS. 1 and 2 show a fundamental construction of a humidity sensing element according to the invention. Reference numeral 10 indicates a metal base which serves as an electrode of this sensing element. The material of the metal base 10 is selected from so-called valve metals such as tantalum, aluminum and titanium. A surface region of the metal base 10 is oxidized by a known anodization process to give a thin layer or film 12 of a dielectric oxide, e.g. tantalum oxide $Ta_2O_5$. Formed on this dielectric oxide film 12 is a semiconductive metal oxide layer 14 which is microscopically porous and gas permeable. Preferably, this layer 14 is made of manganese dioxide $MnO_2$, lead oxide $PbO$ or ruthenium oxide $RuO_2$, or a mixture of two (or even three) of these metal oxides. The metal oxide layer 14 is formed by wetting the anodized metal base with a solution of a thermally decomposable salt of Mn, Pb or Ru, e.g. manganese nitrate, and heating the wetted metal body so as to cause thermal decomposition of the salt dissolved in the solution to a semiconductive oxide such as manganese dioxide. The outer surface of the semiconductive metal oxide layer 14 is covered, either entirely or partly, with an electronically conducting layer 17 which serves as a counter-electrode to the electrode 10. The conducting layer 17 is microscopically porous and gas permeable and has a double-layer structure consisting of an inner layer 16 made of fine particles of carbon and an outer layer 18 which comprises fine particles of a metal dispersed in a solidified organic high polymer. The counter-electrode layer 17 is formed by first applying a commercially available colloidal graphite (an aqueous dispersion) to the surface of the semiconductive metal oxide layer 14, followed by drying, and then coating the carbon layer 16 with a commercially available metal paint such as a silver paint, which is a dispersion of finely powdered silver in an organic dispersion medium comprising a synthetic resin, followed by heating to solidify the dispersion medium.

Macroscopically, the semiconductive metal oxide layer 14 is in close contact with the dielectric oxide film 12 over the entire area of the semiconductive layer 14. Microscopically, however, a real contact between the dielectric oxide film 12 and the semiconductive oxide layer 14 is established only in a multiplicity of small regions 12a which are distributed throughout the apparent or macroscopical interface between these two layers 12 and 14, so that the outer surface of the dielectric oxide film 12 is left uncoated in a multiplicity of regions 12b which also are distributed throughout the aforementioned interface. Therefore, numerous and microscopically small spaces 13 are defined between the outer surface of the dielectric oxide film 12 and the inner surface of the semiconductive metal oxide layer 14.

The device of FIG. 1 functions as a humidity sensing element on the following principle.

When this device is disposed in an atmosphere containing no moisture, there occurs no adsorption of moisture in the porous semiconductive metal oxide layer 14, so that the device provides a constant electrostatic capacitance determined by the kind and geometry of the dielectric oxide film 12 and the total area of the real contact faces 12a. Under this condition, the semiconductive metal oxide layer 14 serves simply as an intermediate electrode to take out the capacitance.

Figure 3:
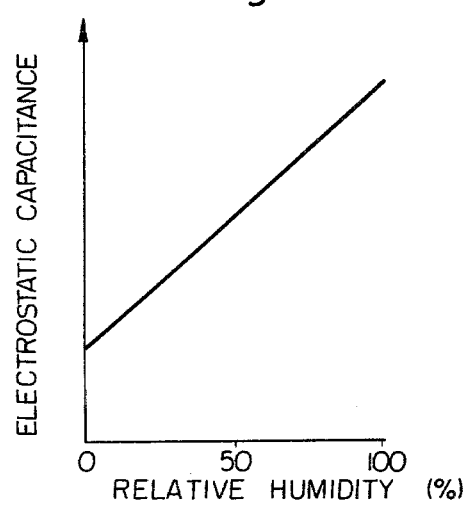
FIG. 3 is a graph showing a general performance of a humidity sensing element according to the invention.

When the same device is disposed in a moist atmosphere, the moisture is adsorbed in the semiconductive metal oxide layer 14, which is gas permeable and hence is hygroscopic, and reaches the coated regions 12a of the surface of the dielectric oxide film 12. Then the adsorbed moisture intrudes into the spaces 13 and spreads over the uncoated regions 12b. Since the quantity of the adsorbed moisture is proportional to the relative humidity in the atmosphere, the degree of moisture covering the surface of the dielectric oxide film 12 is proportional to the relative humidity. The adsorbed moisture is not pure water but contains carbon dioxide contained in air and metal ions such as manganese ions derived from the semiconductive metal oxide layer 14 as well as other impurities originated from the components of the atmosphere. Accordingly the adsorbed moisture serves as an electrolyte having a good conductivity. Under this condition, not only the real contact faces 12a but also a moistened portion of the uncoated regions 12b of the surface of the dielectric oxide film 12 participates in the takeout of electrostatic capacitance from the dielectric oxide film 12. Thus a change in relative humidity in the atmosphere can be detected by a change in the electrostatic capacitance of the device of FIG. 1. As a matter of advantage, a linear relation holds between the relative humidity in an atmosphere surrounding a device of the FIG. 1 type and the electrostatic capacitance of the device over a wide range of relative humidity as shown qualitatively in FIG. 3.

As will be understood from the foregoing general description, important characteristics of a humidity sensing element of the construction of FIG. 1 such as responsiveness to changes in relative humidity, stability of the relation between relative humidity and capacitance and service life at relatively high temperatures, depend principally on the structure of the semiconductive metal oxide layer 14 and the manner of contact of this layer 14 with the dielectric oxide film 12 and the moisture adsorbing property of the semiconductive metal oxide layer 14 and the counter-electrode layer 17. The inventors of the present application have discovered that the structure of the semiconductive metal oxide layer 14 and the manner of contact of this layer 14 with the dielectric oxide film 12 can be optimized by subjecting the humidity sensing element of FIG. 1 to a damping treatment at an elevated temperature, and, in addition, have found optimum process conditions for forming the respective layers 12, 14, 16 and 18 in FIG. 1. The process conditions and the final treatment according to the invention will be described hereinafter in detail in sequence of steps during production of the humidity sensing element. In the following description, tantalum is taken as the material of the metal base 10 and manganese dioxide as the material of the semiconductive oxide layer 14.

Figure 4:
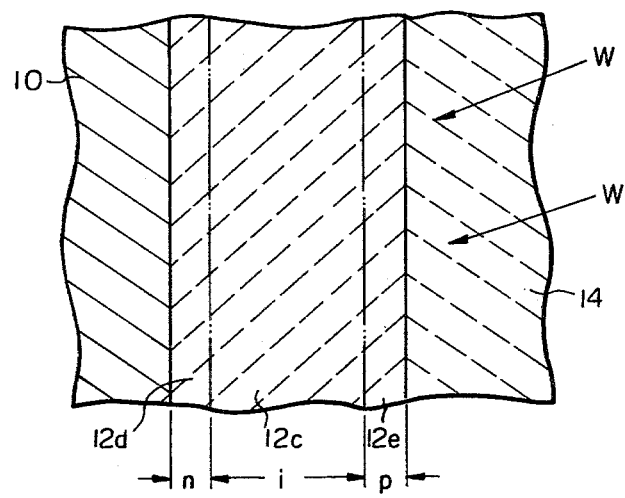
FIG. 4 is an explanatory illustration of a humidity-sensitive layer in a sensing element according to the invention.

Referring to FIG. 4, the tantalum film 12 formed by anodization of a surface region of the tantalum base 10 has a thickness ranging from about 200 A to about 2000 A depending on the anodizing conditions. This film 12 is highly dielectric (has a dielectric constant $\epsilon$ of about 20 to 30) and high in dielectric breakage strength. Under a moisture adsorbing (and desorbing) action of the porous manganese dioxide layer 14, the tantalum oxide film 12 makes a response to a change in the humidity in the exterior atmosphere as a change in the magnitude of electrostatic capacitance the film 12 provides. The origin of the sensitiveness of the dielectric oxide film 12 to moisture may be explained as follows.

In strictness, the tantalum oxide film 12 is not uniformly oxidized over its entire thickness by reason of the relation between the mobility of oxygen ions and that of tantalum ions during the anodization process to form this film 12. A central region 12c of this film 12 is a stoichiometrically oxidized insulating layer, i.e. a $Ta_2O_5$ layer. However, an innermost region 12d (adjacent the unoxidized region of the tantalum base 10) of the dielectric oxide film 12 contains excess tantalum and accordingly should be expressed by $TaO_n$, where n is smaller than 2.5. Therefore, this region 12d is an n-type semiconductor layer. On the other hand, an outermost region 12e of the film 12 contains excess oxygen supplied from an electrolyte solution used in the anodization process, meaning that this region should be expressed by $TaO_m$, where m is larger than 2.5. Therefore, this region 12e is a p-type semiconductor layer. Thus the tantalum oxide film 12 has a p-i-n type multi-layer structure, wherein the central i-type layer 12c serves as a dielectric layer while the outermost p-type layer 12e containing excess oxygen posseses the function of reversely adsorbing moisture (indicated by arrows W in FIG. 4) permeated through the manganese dioxide layer 14 and desorbing the once adsorbed moisture. It is a matter of importance, therefore, to form the tantalum oxide film 12 such that the active surface region 12e acquires a good hydrophilic property and becomes adequate in thickness relative to the dielectric layer 12c.

Figure 5:
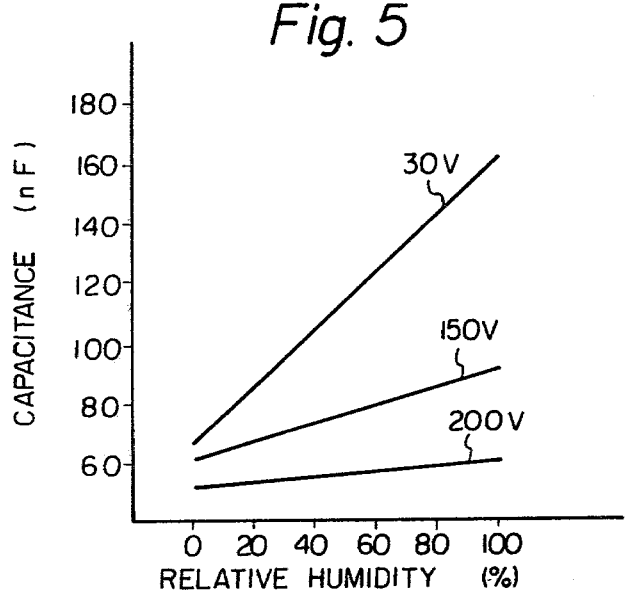
FIGS. 5–15, 17 and 19–22 are graphs showing the influences of various factors in the production of humidity sensing elements having the construction of FIG. 1 of the performance of the product.

We have confirmed experimentally that the magnitude of a change in the electrostatic capacitance of a humidity sensing element of FIG. 1 in response to a certain change in the relative humidity in the exterior atmosphere depends significantly on the magnitude of anodization voltage for forming the tantalum oxide film 12 and progressively diminishes as the anodization voltage is raised. FIG. 5 demonstrates this tendency. The reason for such influence of the anodization voltage on the sensitivity of this humidity sensing element is a fact that the thickness ratio of the active surface layer 12e of the tantalum oxide film 12 to the dielectric layer 12c depends on the anodization voltage. As is well known, the total thickness of the tantalum oxide film 12 depends primarily on the magnitude of the anodization voltage. It is commonly accepted that the tantalum oxide film 12 is formed to a thickness of 16.4 A per 1 volt of anodization voltage, and it is reported by Sasaki, "J. Phys. Chem. Solids", Vol. 13, 177 (1960), that the p-type layer 12e has a constant thickness of 20–50 A irrespective of the magnitude of anodization voltage within a practical range. Accordingly the thickness ratio of the p-type layer 12e to the dielectric layer 12c lowers with increase in anodization voltage: at an anodization voltage of 200 V, the thickness ratio becomes (20~50)/3280, i.e. 0.006~0.015. The tantalum oxide film 12 with such a small thickness of the active surface layer 12e (relative to the dielectric layer 12c) is almost insensitive to changes in humidity as can be seen in FIG. 5. However, the thickness ratio of the active layer 12e to the dielectric layer 12c and hence the sensitivity of the humidity sensing element can be raised by lowering the anodization voltage. In the present invention, therefore, it is preferred to anodize the tantalum body 10 in a usual acid solution at a voltage not higher than 150 volts.

Figure 6:
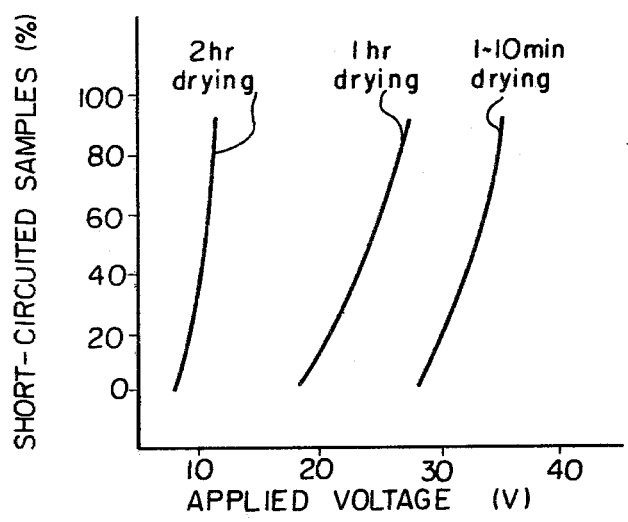
Figure 7:
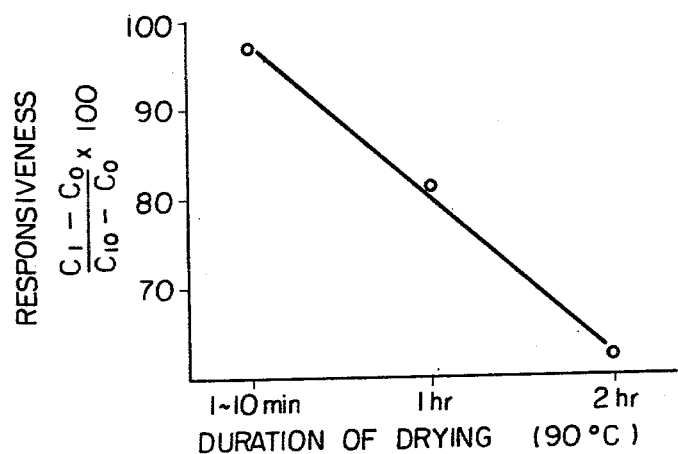

The dielectric oxide film 12 formed by anodization is washed with water to remove the acid solution retained on the anodized surface and thereafter dried to evaporate the water used for washing. We have recognized that the manner of drying after washing of the dielectric film 12 influences the physical property of the surface of the dielectric film 12. When the dielectric film 12 is exposed to a dry and excessively hot air for an unduly long period of time, the dielectric film 12 assumes a water repelling property and therefore cannot be well wetted with an aqueous solution of manganese nitrate used to form the manganese dioxide layer 14. As the result, the dielectric oxide film 12 cannot be uniformly covered with the manganese dioxide layer 14, and, in an extreme case, a considerably large area of the dielectric oxide film 12 is left uncoated. Since the manganese dioxide layer 14 serves also the function of enhancing the dielectric breakdown voltage of the dielectric oxide film 12, an insufficient covering of the dielectric oxide film 12 with the manganese dioxide layer 14 results in insufficiency of the dielectric strength of the humidity sensing element. FIG. 6 shows the result of an experiment to examine the influence of the duration of drying (at 90° C.) of the washed dielectric oxide film 12 on the dielectric strength of the humidity sensing element. Moreover, excessive drying of the dielectric oxide film 12 significantly impairs the responsiveness of the humidity sensing element to changes in humidity in a surrounding atmosphere because the excessively dried surface, i.e. the active layer 12e in FIG. 4, becomes water repelling and less susceptive to moisture. An experimental result demonstrating the influence of the duration of drying of the dielectric film 12 on the responsiveness of the humidity sensing element is shown in FIG. 7. In the experiment, each sample was initially maintained in a 100% RH atmosphere and abruptly transferred into a 0% RH atmosphere to examine desorption responsiveness of the sample. The responsiveness is expressed by the ratio $(C_1-C_0)/(C_{10}-C_0)$, where $C_0$ represents the electrostatic capacitance of the sample measured in the 100% RH atmosphere, $C_1$ represents the capacitance measured after the lapse of 1 minute from the transfer of the sample into the 0% RH atmosphere, and $C_{10}$ represents the capacitance 10 minutes after the transfer. As a conclusion deduced from the results of numerous experiments including one presented in FIG. 7, it is preferable to dry the washed dielectric oxide film 12 in air, which may be circulated, for a period of about 1 min to about 10 min at a temperature in the range from 20° to 90° C.

Manganese dioxide, lead oxide and ruthenium oxide are semiconductive metal oxides suitable for a humidity sensing element according to the invention in view of their electrical conductivity, ability of reforming the dielectric oxide film 12 and ability of adsorbing and desorbing moisture when used in the form of a porous layer. If desired, the semiconductive metal oxide layer 14 may comprise two, or even all, of these three semiconductive metal oxides. In the present invention, it is highly preferable to use an aqueous solution of manganese nitrate to form manganese dioxide by pyrolysis, to use an aqueous solution of lead nitrate to form lead oxide, and to use an aqueous solution of either ruthenium nitrate or ruthenium trichloride to form ruthenium oxide. After the steps of anodization, washing and drying, the metal body formed with the dielectric oxide film 12 is wetted with an aqueous solution of a selected metal salt (or salts), and the wetted body is heated in air at a temperature suitable for thermal decomposition of the metal salt to an intended oxide.

Where the semiconductive metal oxide layer 14 is of manganese dioxide, it is most preferable to form this layer 14 by pyrolysis of an aqueous solution of manganese nitrate. In this case the thickness of the manganese dioxide layer 14 becomes larger as the concentration of the manganese nitrate solution is raised. The concentration of the solution can be represented by the density of the solution. When the manganese dioxide layer 14 is formed to an excessively larger thickness, the moisture-sensitive surface of the dielectric oxide film 12 is covered nearly completely with a thick and dense layer 14 of manganese dioxide. In such a state, the dielectric oxide film 12 hardly exhibits changes in capacitance in response to changes in humidity, and, besides, the thick manganese dioxide layer 14 is no longer effective in quick and smooth adsorption-desorption of moisture.

Figure 8:
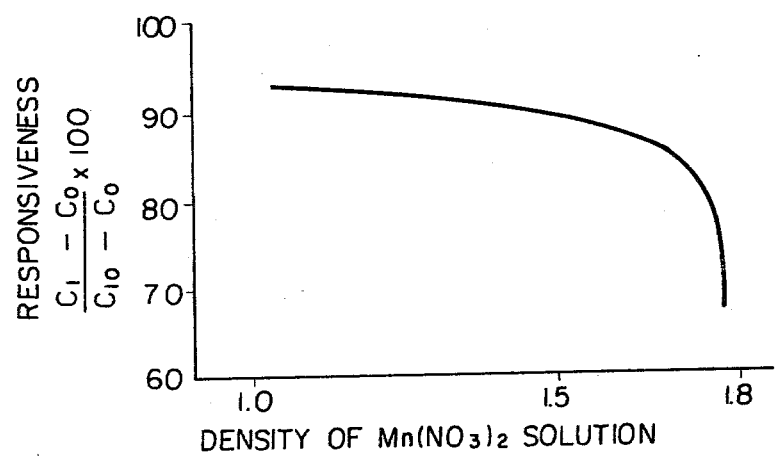
Figure 9:
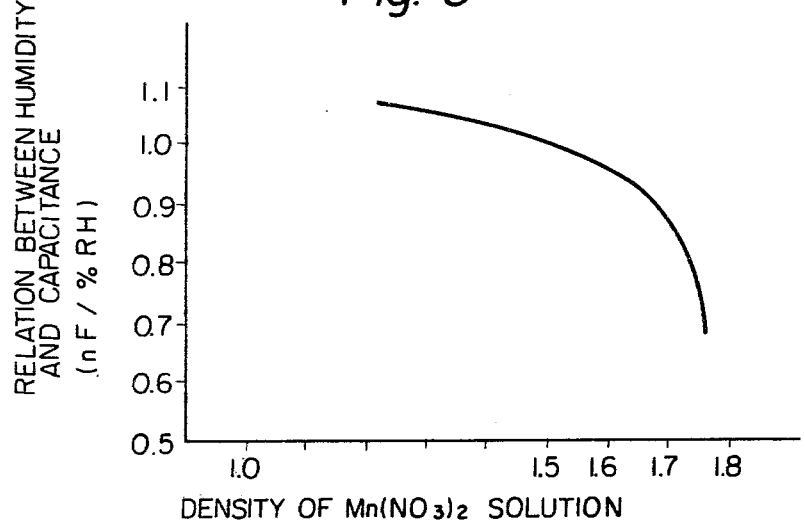

FIG. 8 shows a variation in the responsiveness, expressed by the above described ratio $(C_1-C_0)/(C_{10}-C_0)$, of the humidity sensing element of FIG. 1 (the body 10 was of tantalum) with respect to the density of a manganese nitrate solution used to form the manganese dioxide layer 14. FIG. 9 shows a variation in the sensitivity of the same humidity sensing element, expressed by the magnitude of a change in electrostatic capacitance per 1% change in relative humidity, with respect to the density of the manganese nitrate solution. As demonstrated by the curves in FIGS. 8 and 9, the use of a manganese nitrate solution having a relatively low density gives a humidity sensing element excellent both in sensitivity and responsiveness, but the sensing element becomes very poor in these characteristics when the density of the solution exceeds 1.7. Accordingly it is highly preferable to use an aqueous solution of manganese nitrate having a density not higher than 1.7 in the production of a humidity sensing element according to the invention.

The gas permeable carbon layer 16 as an inner part of the counter- or collector-electrode layer 17 is formed most preferably by the application of a colloidal graphite, i.e. a dispersion of very fine particles of graphite in an aqueous medium which may contain ammonia as dispersant and a small amount of binder such as carboxymethyl cellulose, onto the manganese dioxide layer 14, followed by drying. For example, such a colloidal graphite is commercially available under the tradename "Aquadag" (Acheson Colloids Company, U.S.A.).

Figure 10:
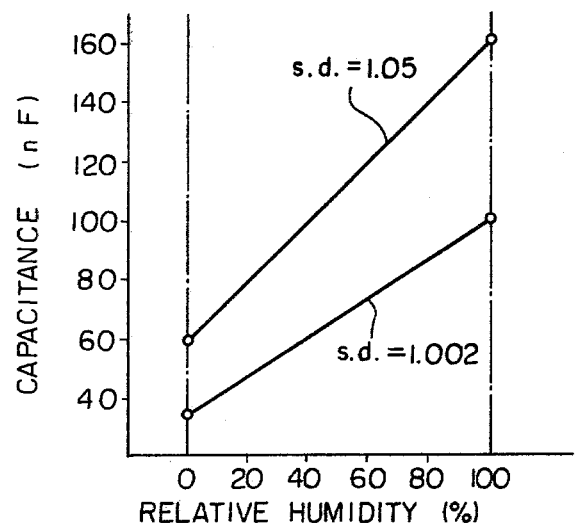
Figure 11:
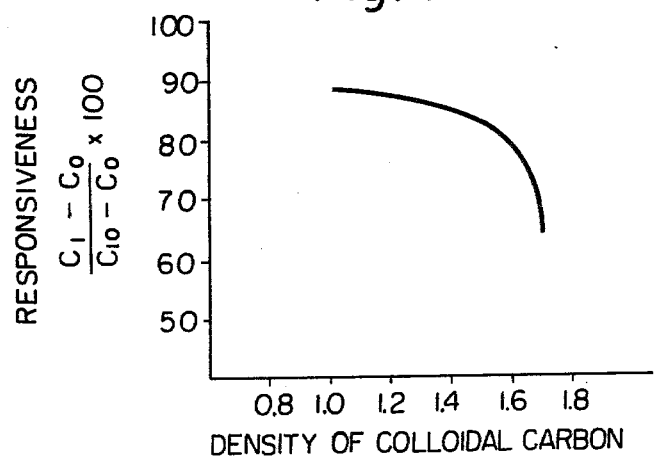

The graphite concentration in a colloidal graphite to form the carbon layer 16, i.e. the density of the colloidal graphite, influences the characteristics of a humidity sensing element according to the invention. FIG. 10 demonstrates the dependence of the capacitance of the humidity sensing element on the density of a colloidal graphite. The capacitance decreases as the density of the colloidal graphite lowers because both the electric resistance of the carbon layer 16 itself and the contact resistance between the manganese dioxide layer 14 and the carbon layer 16, and, as a consequence, the absolute value of the capacitance taken out through the carbon layer 16 becomes small. However, the use of a colloidal graphite having a very high density results in that the carbon layer 16 is formed to an excessively large thickness and adversely influences the sensitivity and responsiveness of the humidity sensing element by the same reasons as described above in regard of the thickness of the manganese dioxide layer 14. FIG. 11 shows the relationship between the density of the colloidal graphite and the responsiveness of the humidity sensing element. Therefore, it is undesirable to use a colloidal graphite having a very high density despite a sufficiently low resistance of the resultant carbon layer 16. To form a carbon layer 16 which is satisfactory both in its property as an electrode layer and in its moisture adsorption-desorption ability, it is preferable to use a colloidal graphite having a density not higher than 1.5.

The metallic layer 18 as an outer part of the gas permeable electrode layer 17 is indispensable for a humidity sensing element according to the invention since this layer 18 makes it possible to apply a solder or to connect leads to the sensing element and, furthermore, ensures the collection of electrostatic capacitance produced in the sensing element. Conveniently this layer 18 is formed by applying a silver paint, i.e. a dispersion of fine particles of silver in a medium comprising a synthetic resin dissolved in an organic solvent, onto the carbon layer 16 and then drying the paint-coated element at an elevated temperature to evaporate the solvent thereby to solidify the resin. Several types of silver paints are on the market, but in the present invention preference is given to a silver paint utilizing an acrylic resin as the principal component of the dispersion medium and another type of silver paint utilizing a fluorocarbon resin. In general, acrylic resins are highly hydrophilic and exhibit moisture adsorption-desorption ability in air with high sensitivity and responsiveness, whereby it is possible to utilize a conductive layer of a solidified silver paint comprising an acrylic resin as a humidity sensing element of a resistance change type. Accordingly a silver paint utilizing an acrylic resin is a very suitable material for the outermost electrode layer 18 in a humidity sensing element of FIG. 1. For example, a silver paint of this type is supplied from E. I. Dupont de Nemours and Company, U.S.A. Fluorocarbon resins, e.g. polytetrafluoroethylene, are excellent in heat resistance and highly resistant to various chemicals. Besides, a mass of a fluorocarbon resin has innumerable micropores. Accordingly a silver paint utilizing a fluorocarbon resin, too, is a highly preferable material for the outermost electrode layer 18 in a humidity sensing element according to the invention. For example, a silver paint of this type is supplied from Acheson Colloids Company under the tradename "Electrodag".

Figure 12:
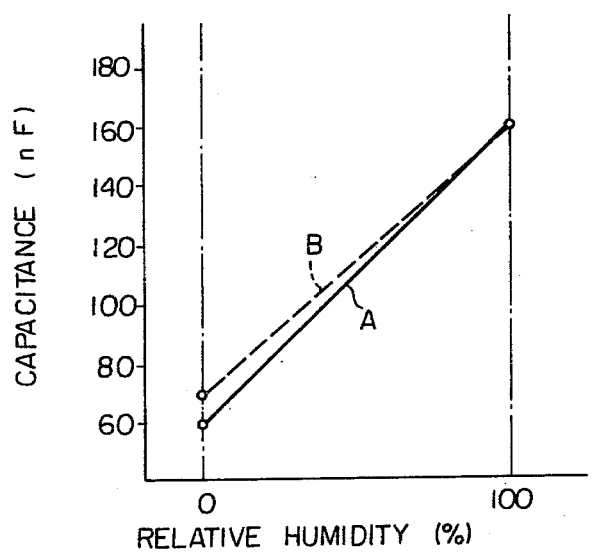

In FIG. 12, the curve A represents the relationship between relative humidity in the atmosphere and the capacitance of a humidity sensing element according to the invention produced by using a silver paint comprising an acrylic resin, and the curve B represents the same for another humidity sensing element also according to the invention but produced by using a silver paint comprising a fluorocarbon resin. As demonstrated by the graph of FIG. 12, the use of a silver paint comprising either an acrylic resin or a fluorocarbon resin to form the outermost electrode layer 18 gives a humidity sensing element which exhibits a linear change in its capacitance with a change in relative humidity in the environment over a wide range of humidity.

Furthermore, we have found that excellent characteristics of a humidity sensing element whose outermost electrode layer 18 is produced as described above can further be improved by treating the sensing element, after drying of the silver paint, with an organic solvent.

There is a possibility that the outermost electrode layer 18 formed by solidifying the silver paint applied onto the manganese dioxide layer 14 at a suitably elevated temperature will not entirely be uniform and stable but will contain a certain amount of non-solidified resin and/or some other impurities. The presence of small amounts of impurities, including non-solidified resin, in this electrode layer 18 will offer little problem if this layer 18 serves merely as an electrically conductive layer. However, this electrode layer 18 is so formed as to have a moisture adsorption-desorption ability and to participate in the susceptibleness of the sensing element to humidity. Besides, it will be probable that impurities contained in the silver paint do not entirely remain in the outermost layer 18 but partly infiltrate into the manganese dioxide layer 14 through the carbon layer 16 before drying of the silver paint. Therefore, the presence of impurities in this layer 18 influences appreciably and adversely the fundamental characteristics of the humidity sensing element such as sensitivity and responsiveness.

Impurities originating from a silver paint can effectively be removed from the humidity sensing element after drying of the silver paint applied thereto by treating the sensing element with an organic solvent, preferably a polar solvent, for a certain period of time. This treatment can be accomplished either by dipping the sensing element in the solvent or by continuously spraying the solvent on the sensing element, but preference is given to the dipping method. Examples of preferable polar solvents for this purpose are ketones such as acetone and methylethyl ketone, carboxylic acids such as formic acid and acetic acid, alcohols, esters such as ethyl acetate, amides such as N-methylformamide, xylenes and halogenated compounds such as chloroform.

Figure 13:
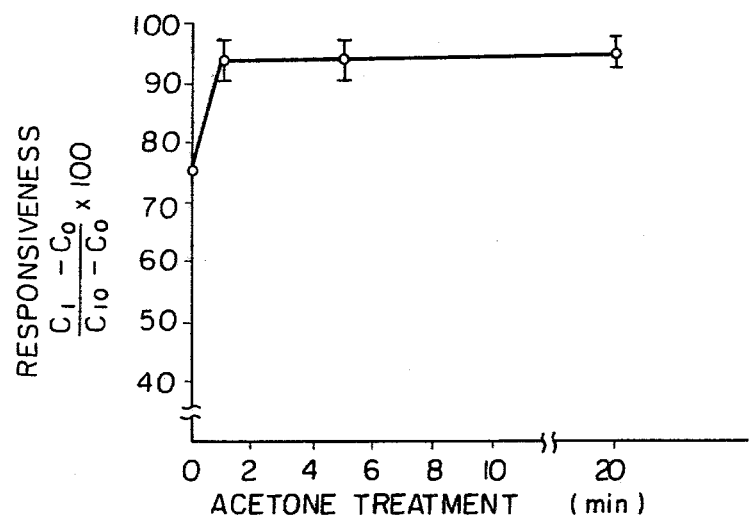

This treatment can be accomplished at room temperature. FIG. 13 shows a variation in the responsiveness of a humidity sensing element produced by a method according to the invention, using a silver paint comprising an acrylic resin, with respect to the duration of dipping of the sensing element in acetone after drying of the applied silver paint. As demonstrated by the graph of FIG. 13, usually it suffices to continue the organic solvent treatment for about 1 minute, and it is preferable that the duration of this treatment ranges from about 20 seconds to about 20 minutes depending on the shape and size of the humidity sensing element.

Figure 14:
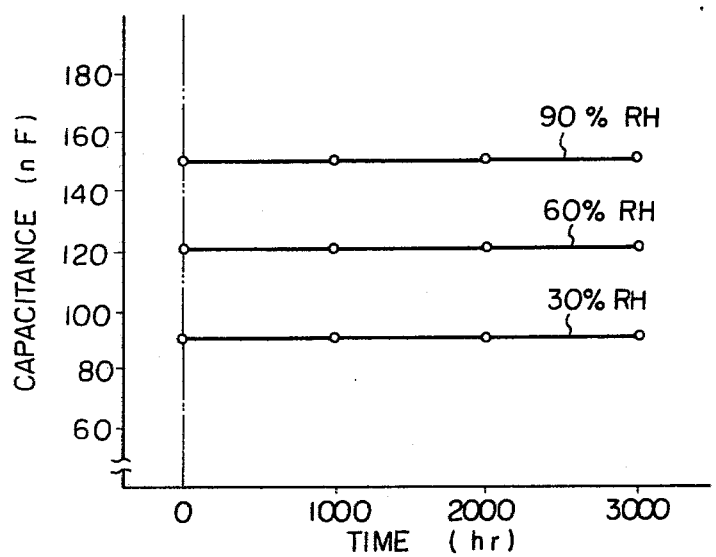

A humidity sensing element according to the invention produced through the above described steps exhibits little change in the relationship between humidity in the environment and electrostatic capacitance of the sensing element with the passage of time insofar as the sensing element is used, or stored, at temperatures around room temperature, i.e. in the range from 10° C. to 30° C. For example, FIG. 14 shows the result of an experiment, in which a humidity sensing element produced through the above described steps was maintained for 3000 hr at room temperature, without particularly conditioning humidity in the environment, and was subjected to measurement of its humidity-capacitance characteristic at regular intervals. Each time, the measurement was accomplished under 20° C.-30% RH condition, 20° C.-60% RH condition and 20° C.-90% RH condition in turn. In FIG. 14, 0 hr on the abscissa means the measurement immediately after completion of the production of the sensing element.

Figure 15:
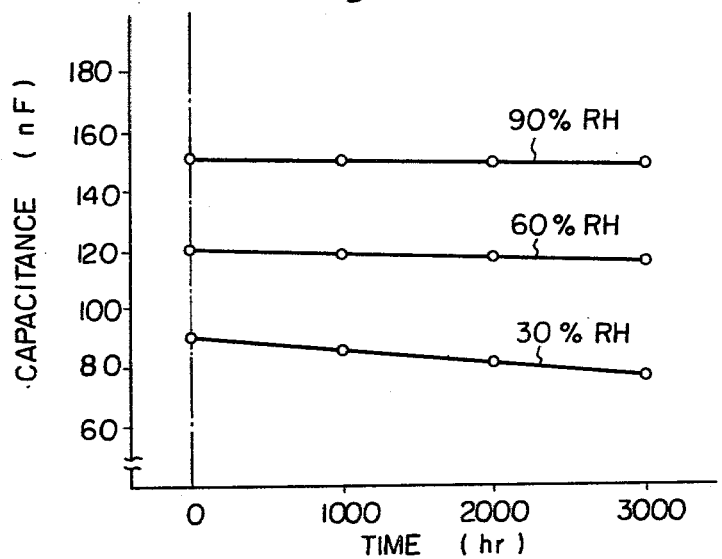

However, when a similarly produced humidity sensing element is kept at higher temperatures the relationship between the humidity and the electrostatic capacitance varies gradually with the passage of time. For example, FIG. 15 shows a result of an experiment which was generally similar to the experiment described with reference to FIG. 14 except that the sensing element was maintained in 50° C.-90% RH atmosphere and that the temperature of the three differently humid atmospheres for the measurement was 50° C. In this case the humidity sensing element exhibited a gradual decrease in its electrostatic capacitance per unit humidity with the passage of time. As can be seen in FIG. 15, this tendency became particularly notable as the humidity lowered, meaning that the sensing element exhibited a change in the manner of dependence of its capacitance on humidity.

The reason for a gradual change in the humidity-capacitance characteristic of the sensing element in a high temperature high humidity atmosphere may be explained as follows.

Figure 16A:
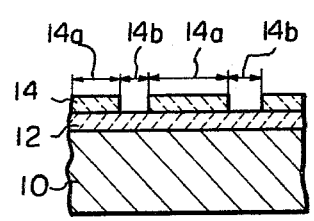
FIGS. 16(A) and 16(B) are explanatory illustrations of moisture adsorbing and humidity-sensitive portions of a sensing element having the construction of FIG. 1, respectively showing two different states before and after a high temperature damping treatment of the sensing element.
Figure 16B:
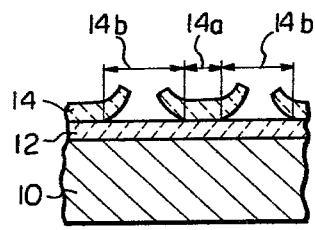

Referring to FIGS. 16(A) and 16(B), when the humidity sensing element is maintained in a hot and humid atmosphere the manganese dioxide layer 14 gradually peels off from the tantalum oxide layer 12 by the influences of the high temperature and the vapor pressure (of moisture). This means a gradual decrease in the total area of contacting regions 14a, where contact is established between the manganese dioxide layer 14 and the tantalum oxide film 12, and naturally a gradual increase in the total area of non-contacting regions 14b. If other factors remain unchanged, a decrease in the area of the contacting regions 14a results naturally in a decrease in the electrostatic capacitance taken out of the humidity sensing element.

According to a method of the invention, the production of a humidity sensing element is not completed by the step of forming the outermost electrode layer 18. It is required that, after forming of the outermost layer 18, i.e. after drying of the applied silver paint (optionally followed by the above described treatment with an organic solvent), the sensing element be subjected to a damping treatment at a sufficiently high temperature. The object of this treatment is to intentionally cause local peeling of the manganese dioxide layer 14 from the tantalum oxide film 12 as illustrated in FIG. 16(B) thereby to allow a decrease in the area of the contacting regions 14a to reach a terminal point. We have thought that the humidity sensing element produced through such a treatment will exhibit good stability even when long used under high temperature high humidity conditions insofar as the treatment is accomplished at a temperature above the upper boundary of a temperature range in which the sensing element is used. This thought has been verified experimentally as will be described hereinafter.

Figure 17:
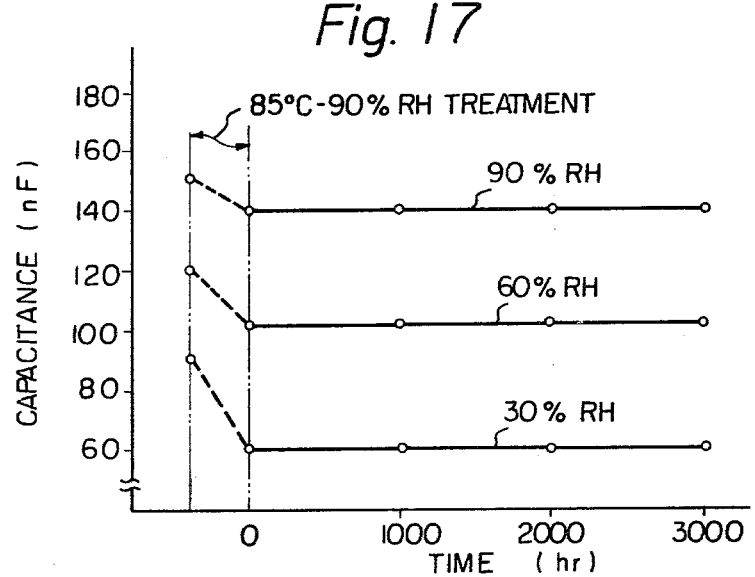

The damping treatment as the final step of a production method according to the invention must be accomplished by exposing the humidity sensing element after the step of forming the outermost electrode layer 18 both to a high humidity and to a high temperature simultaneously. A first embodiment of such a treatment is to maintain the humidity sensing element in a high temperature high humidity atmosphere (vapor phase) for a relatively long amount of time. For example, FIG. 17 shows the effect of a 30 hr damping treatment in 85° C. 90% RH atmosphere on a humidity sensing element identical with those used in the experiments of FIGS. 14 and 15. The treatment caused a sharp decrease in the electrostatic capacitance of the sensing element. After the treatment, however, the sensing device exhibited little change in its capacitance (at a definite humidity) during 3000 hr maintenance thereof under 50° C.-90% RH condition. Similarly little change in the capacitance was observed when the sensing element subjected to the damping treatment was long maintained in room temperature atmosphere, in 85° C. dry atmosphere or 85° C.-90% RH atmosphere.

Figure 18A:
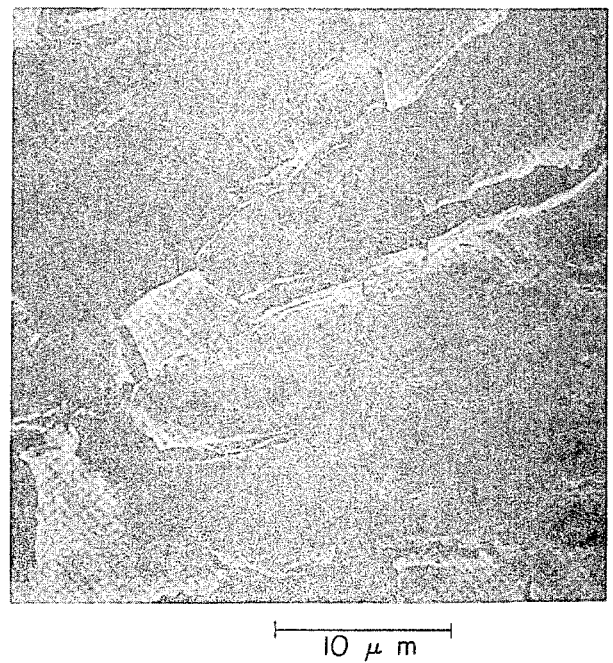
FIGS. 18(A) and 18(B) are electron microscope microphotographs of a semiconductive metal oxide layer in a humidity sensing element of the construction of FIG. 1, respectively showing two different states before and after a high temperature damping treatment of the humidity sensing element.
Figure 18B:
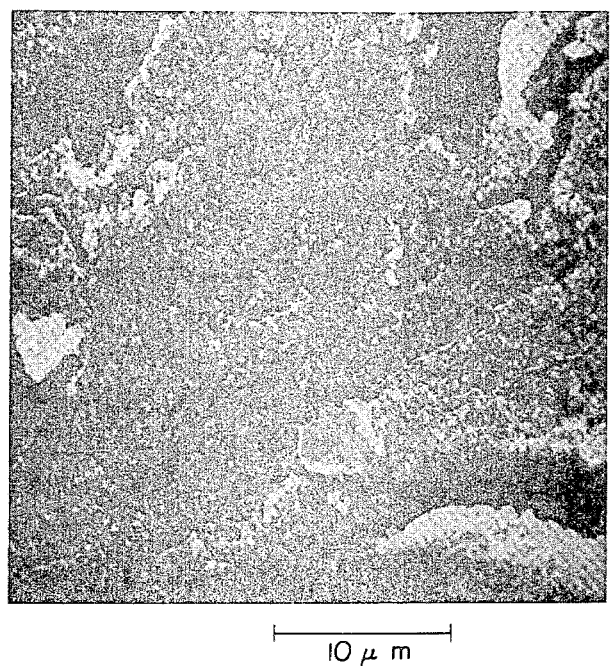

FIG. 18(A) is a 3000 magnification microphotograph (taken with a scanning electron microscope) of a manganese dioxide layer formed on a tantalum oxide film during production of a humidity sensing element by a method of the invention, and FIG. 18(B) is a 3000 magnification microphotograph of a manganese dioxide layer which is formed similarly but thereafter subjected to a damping treatment for 30 hr in 85° C.-90% RH atmosphere. As can be seen in FIG. 18(B), the damping treatment produced a multiplicity of microscopic crevices in the manganese dioxide layer as the result of local peeling of this layer from the tantalum oxide film with decrease in the area of the contacting regions 14a in FIGS. 16(A) and 16(B). When the damping treatment is accomplished at a humidity above 90% RH, the degree of such peeling of the manganese dioxide layer from the tantalum oxide film, i.e. the extent of decrease in the area of the contacting regions 14a, depends on the temperature for the treatment: the area of the contacting regions 14a decreases more and more as the temperature for the treatment is made higher. In the case of accomplishing the damping treatment in a high temperature high humidity atmosphere (vapor phase treatment), it is preferable that the relative humidity of the treatment atmosphere is at least 90% while the temperature of this atmosphere is higher than the upper boundary of a temperature range in which the humidity sensing element is used. More practically, the temperature for the damping treatment is preferably above 80° C. and more preferably above 85° C. The upper limit to the temperature for the damping treatment is a temperature at which the humidity sensing element becomes inoperative.

Figure 19:
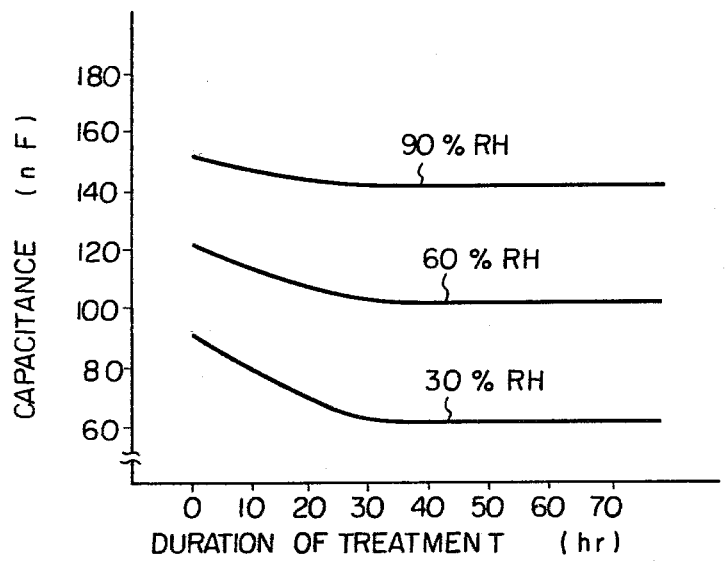

When the damping treatment is accomplished in a high temperature high humidity atmosphere, an important factor other than the temperature and humidity is the duration of the treatment. If the duration is insufficient the decrease in the area of the contacting regions 14a of the manganese dioxide layer does not reach a terminal point. When the treatment is accomplished in 85° C.-90% RH atmosphere, the relationship between the duration of the treatment and the capacitance of the treated humidity sensing element becomes as shown in FIG. 19. The capacitance measured at a constant humidity decreases gradually as the duration of the treatment is extended but becomes minimal and stabilizes when the duration reaches about 30 hr. The minimum duration of the treatment needed to stabilize the humidity-capacitance characteristic of the sensing element depends on various factors such as the temperature for the damping treatment, thickness of the manganese dioxide layer, and the shape and size of of the sensing element, but it was confirmed that a vapor phase damping treatment should be continued for at least 30 hr, and more preferably for at least 50 hr.

Figure 20:
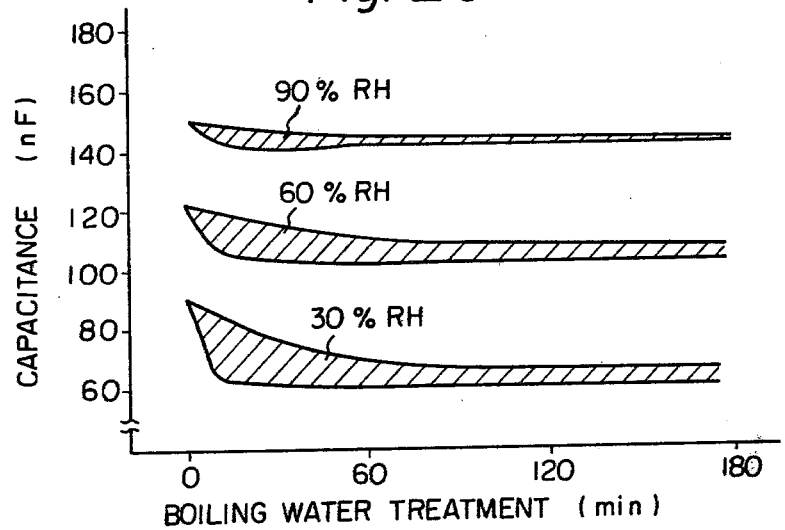

A second embodiment of a high temperature damping treatment according to the invention is the immersion of the nearly finished humidity sensing element in boiling water. This liquid phase treatment may be taken as equivalent to the maintenance of the sensing element in 100° C. -100% RH atmosphere. However, the liquid phase treatment has a practically important advantage that the local peeling of the manganese dioxide layer from the tantalum oxide film is greatly accelerated, so that, as shown in FIG. 20, a liquid phase treatment of the sensing element in boiling water for a period of 10-180 minutes corresponds in effect to a vapor phase treatment for a period of 30–50 hours in, for example, 85° C.-90% RH atmosphere.

Figure 21:
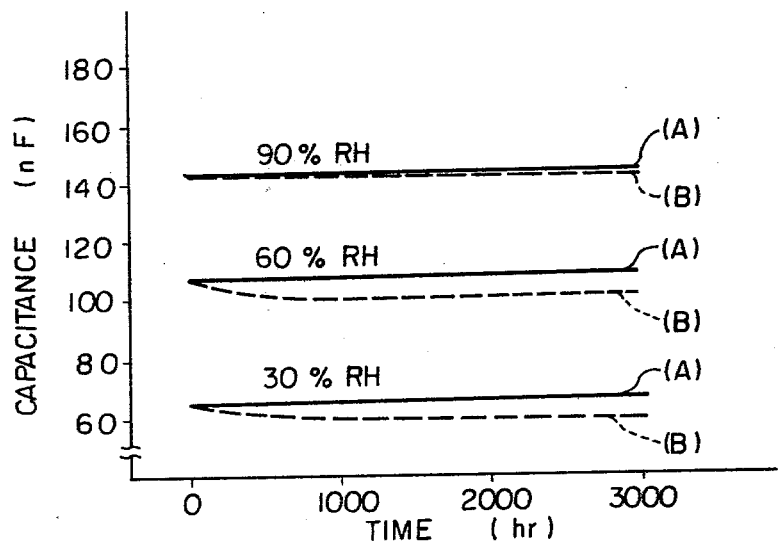

Sometimes, however, the stabilizing effect of the boiling water treatment is slightly inferior to that of the vapor phase treatment depending on the shape and size of the humidity sensing element subject to treatment. FIG. 21 shows the result of an experiment similar to the experiments described with reference to FIGS. 14 and 15 to examine changes in capacitance of the humidity sensing elements treated in boiling water for 30 minutes. Other than this treatment, the samples for this experiment were produced similarly to those used in the experiments illustrated in FIGS. 14 and 15. The curves (A) in FIG. 21 represent capacitance values of a sample maintained at room temperature and curves (B) capacitance values of another sample maintained under 80° C.-90% RH. The temperature of the three differently humid atmospheres for the measurement was 80° C. As is apparent, the tested sensing elements exhibited certain changes in capacitance with the passage of time when used in a hot and humid atmosphere though they exhibited practically no change when used at room temperature.

Figure 22:
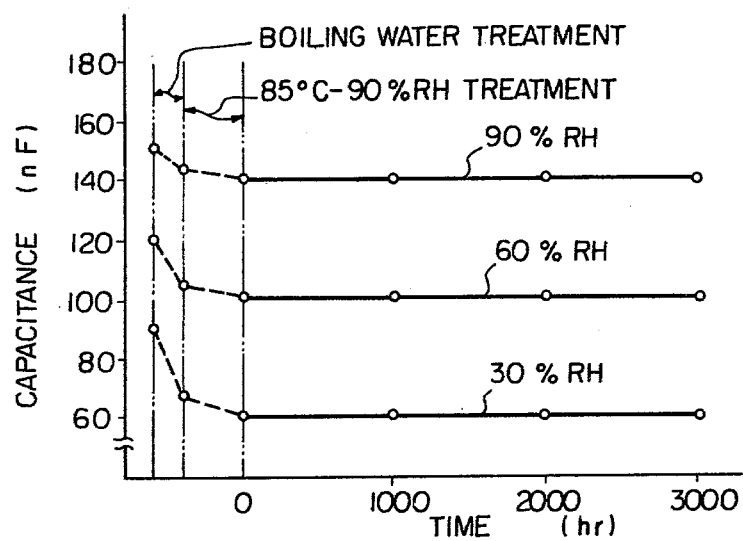

We have confirmed that a humidity sensing element (according to the invention) which does not exhibit an appreciable change in the relationship between the humidity and the capacitance even when used long in a hot and humid atmosphere can be obtained by adding the hereinbefore described vapor phase damping treatment to the above described boiling water treatment. As an advantage of this method over the damping treatment solely in vapor phase, the total duration of the boiling water treatment and the succeeding vapor phase treamment can be shortened considerably than the minimum duration necessary to the damping treatment solely in vapor phase. In the combined treatment method, a major part of a stabilizing process which requires at least 30 hr treatment in a high temperature high humidity atmosphere can be attained with acceleration by the initial boiling water treatment, and a possible insufficiency of stabilization by the boiling water treatment can be remedied by the succeeding vapor phase treament. Accordingly the vapor phase treament in this method can be completed in a considerably shorter time compared with the treatment solely in vapor phase. In view of experimental results including one presented in FIG. 20, it is preferably to continue the boiling water treatment in the combined treatment method for a period of 10 to 60 minutes depending on the shape and size of the humidity sensing element. The succeeding vapor phase treatment is accomplished preferably at a relative humidity not lower than 90% and at a temperature above the upper boundary of a temperature range in which the humidity sensing element is used, and more preferably at a temperature above 80° C. It is preferable that the duration of this vapor phase treatment is at least 1 hour and is less than 30 hours. FIG. 22 shows an experimental result demonstrating the effect of the combined treatment method. The experiment was carried on a humidity sensing element produced similarly to those used in the experiments of FIGS. 14 and 15 then subjected to the combined damping treatment. The boiling water treatment was completed in 30 minutes, and the succeeding vapor phase treatment was accomplished for 10 hours in 85° C.-90% RH atmosphere. The treated sensing element was maintained in 80° C.-90% RH atmosphere, and the temperature of the three differently humid atmospheres for the measurement was 80° C.

As will be understood from the foregoing description with reference to FIGS. 14–22, a high temperature damping treatment of a humidity sensing element after the step of forming the outermost electrode layer 18 during a production method according to the invention is indispensable to the production of a humidity sensing element which is in accordance with the present invention and is fully satisfactory in its stability and reliability as well as fundamental humidity-sensing abilities. With regard to the construction or structure of the humidity sensing element, the effect of the high temperature damping treatment appears as the microscopical crevices in the semiconductive metal oxide layer.

The following example further illustrates the present invention.

EXAMPLE

Figure 23:
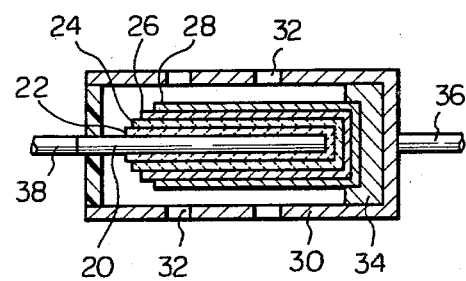
FIG. 23 is a sectional view of a humidity sensor whose sensing element is an embodiment of the present invention.

Referring to FIG. 23, a tantalum rod 20 (1 mm in diameter and 10 mm in length) was anodized in a 0.1 mol/liter phosphoric acid solution at room temperature to an anodization voltage of 50 V to form a tantalum oxide film 22 on the surface of the rod 20. The anodized rod 20 was washed with water and then exposed to 90° C. hot air for 1 min to remove moisture from the anodized surface 22. Then the anodized rod was dipped in an aqueous solution of manganese nitrate having a density of 1.2 at room temperature, and the wetted rod was heated in air at 300° C. to form a manganese dioxide layer 24 by thermal decomposition of the manganese nitrate on the tantalum oxide film 22. Thereafter, the manganese dioxide coated rod was subjected to a usual reforming process which was performed by the application of a voltage of 50 V in a 1 mol/liter aqueous solution of oxalic acid. Thereafter, a carbon layer 26 was formed on the manganese dioxide layer 24 by using a colloidal graphite (of Acheson Colloids Company) having a density of 1.05, and a conductive layer 28 was formed on the carbon layer 26 by the application of a silver paint (of Dupont) comprising an acrylic resin. After drying of the silver paint 28, the semifinished element was immersed in acetone for 1 min. The thus constructed element was encased in a metal case 30, and a gap between the silver paint layer 28 and the case 30 was filled up with a solder 34 over a limited area. The case 30 had vent holes 32 so that the sensing element could be exposed to the atmosphere. Indicated at 36 and 38 are leads connected to the encased sensing element.

Figure 24:
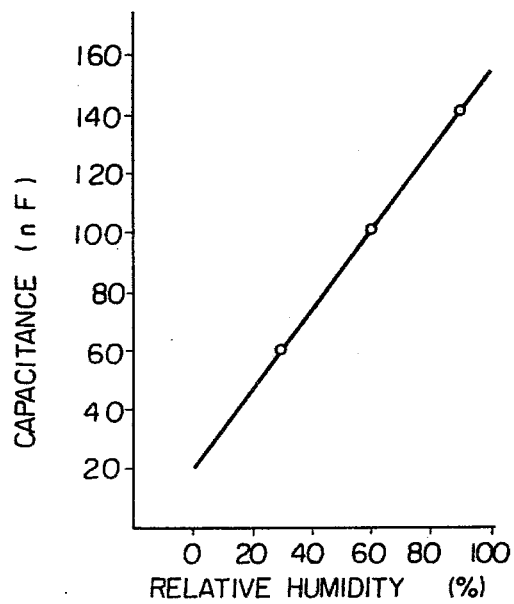
FIG. 24 is a graph showing a fundamental performance of a humidity sensor which has the construction of FIG. 23 and is an example of sensors utilizing a sensing element according to the invention.

The encased sensing element was subjected to a high temperature damping treatment, which was accomplished in 50° C.-90% RH atmosphere for 35 hr. The humidity sensing element produced in this example was excellent in sensitivity, responsiveness and stability. FIG. 24 shows the relationship between relative humidity in the environment and the electrostatic capacitance of this sensing element.

What is claimed is:

1. A method of producing a humidity sensing element of a capacitance change type, the method comprising the steps of:
  (a) anodizing a valve metal body to form a dielectric oxide layer film on a surface of said metal body;
  (b) forming a semiconductive metal oxide layer which is gas-permeable on said dielectric film by thermal decomposition of an aqueous solution comprising a thermally decomposable metal salt applied to said dielectric oxide film;

(c) forming a gas-permeable layer of carbon on at least a portion of the outer surface of said semiconductive metal oxide layer;

(d) forming a gas-permeable and electronically conductive layer on said layer of carbon by applying a paint comprising a metal powder and a synthetic resin as a binder to the outer surface of said layer of carbon; and (e) subjecting the product of step (d) to a vapor phase treatment for a period not shorter than 30 hours at a relative humidity of not lower than 90% at a temperature not lower than 80° C.

2. A method of producing a humidity sensing element of a capacitance change type, the method comprising the steps of:

(a) anodizing a valve metal body to form a dielectric oxide layer film on a surface of said metal body;

(b) forming a gas-permeable, semiconductive metal oxide layer on said dielectric film by thermal decomposition of an aqueous solution comprising a thermally decomposable metal salt applied to said dielectric oxide film;

(c) forming a gas-permeable layer of carbon on at least a portion of the outer surface of said semiconductive metal oxide layer;

(d) forming a gas-permeable and electronically conductive layer on said layer of carbon by applying a paint comprising a metal powder and a synthetic resin as a binder to the outer surface of said layer of carbon; and (e) immersing the product of step (d) in boiling water for a predetermined period of time ranging from 10 to 180 minutes.

3. A method of producing a humidity sensing element of a capacitance change type, the method comprising the steps of:

(a) anodizing a valve metal body to form a dielectric oxide layer film on a surface of said metal body;

(b) forming a gas-permeable, semiconductive metal oxide layer on said dielectric film by thermal decomposition of an aqueous solution comprising a thermally decomposable metal salt applied to said dielectric oxide film;

(c) forming a gas-permeable layer of carbon on at least a portion of the outer surface of said semiconductive metal oxide layer;

(d) forming a gas-permeable and electronically conductive layer on said layer of carbon by applying a paint comprising a metal powder and a synthetic resin as a binder to the outer surface of said layer of carbon; and (e) subjecting the product of step (d) to a combination of treatments which comprises immersing said product in boiling water for a period of from 10 to 60 minutes and maintaining the thus treated product in a vapor phase atmosphere for a period of not shorter than 1 hour but shorter than 30 hours at a relative humidity of not lower than 90% and at a temperature not lower than 80° C.

4. A method according to claim 1, 2 or 3, wherein an anodization voltage to accomplish step (a) is not higher than 150 volts.

5. A method according to claim 4, wherein said aqueous solution is a solution of manganese nitrate and has a density not higher than 1.7.

6. A method according to claim 1, 2 or 3, wherein said aqueous solution is a solution of at least one thermally decomposable salt selected from the group consisting of manganese nitrate, lead nitrate, ruthenium nitrate and ruthenium trichloride.

7. A method according to claim 1, 2 or 3, wherein step (c) is accomplished by applying an aqueous dispersion of colloidal particles of carbon onto at least a portion of the outer surface of said semiconductive metal oxide layer and thereafter drying said aqueous dispersion applied onto said semiconductive metal oxide layer, the density of said aqueous dispersion being not higher than 1.5.

8. A method according to claim 1, 2, or 3, wherein said paint comprises as said binder at least one synthetic resin selected from the group consisting of an acrylic resin and a fluorocarbon resin.

9. A method according to claim 8, wherein said metal powder in said paint is of at least one metal selected from the group consisting of silver, gold, platinum, copper and aluminum.

10. A method according to claim 1, 2, or 3, further comprising the step of washing the product of step (a) with water to remove an anodizing liquid used in step (a) from said dielectric oxide film and then exposing the washed product to a clean gas atmosphere thereby to evaporate a portion of moisture present on and in said dielectric film prior to step (b).

11. A method according to claim 10, wherein said clean gas atmosphere is air of which temperature is in the range from 20° to 90° C., the washed product being exposed to said air for a period of time ranging from 1 minute to 10 minutes.

12. A method according to claim 1, 2, or 3, further comprising the step of treating the product of step (d) with an organic solvent for a predetermined period of time prior to step (e).

13. A method according to claim 12, wherein said predetermined period of time ranges from 20 seconds to 20 minutes, said organic solvent being a polar solvent.

14. A method according to claim 13, wherein said organic solvent consists of at least one organic compound selected from the group consisting of ketones, carboxylic acids, esters, alcohols, amides, xylenes and halogenated organic compounds.

* * * * *